(12) United States Patent
Horvath

(10) Patent No.: US 6,284,766 B1
(45) Date of Patent: Sep. 4, 2001

(54) 9H-PYRIMIDO [4,5-B] INDOLE DERIVATIVES: CRF1 SPECIFIC LIGANDS

(75) Inventor: Raymond F. Horvath, North Branford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/561,569

(22) Filed: Apr. 28, 2000

Related U.S. Application Data

(60) Provisional application No. 60/131,719, filed on Apr. 30, 1999.

(51) Int. Cl.[7] ............... A01N 43/54; A61K 31/505; C07D 239/00; C07D 471/00; C07D 487/00
(52) U.S. Cl. ................................ 514/267; 544/250
(58) Field of Search ..................... 514/267; 544/250

(56) References Cited

FOREIGN PATENT DOCUMENTS

| 98/29397 | * | 7/1998 | (WO) . |
| WO 98/29397 A | | 7/1998 | (WO) . |
| WO 99/51597 A | | 10/1999 | (WO) . |
| WO 99/51598 A | | 10/1999 | (WO) . |
| WO 99/51600 A | | 10/1999 | (WO) . |

OTHER PUBLICATIONS

Müller et. al., "Deaza–2–phenyladenines: . . . ", J. Med. Chem., Oct. 1990, vol. 33, No. 10, pp. 2822–2828.*
Arzneim.–Forsch. 1978, 28, pp. 1056–1065 (with translation attached).
Khim. Geterotsikl. Soedin. 1991, 6, p. 852 (with translation attached).

* cited by examiner

Primary Examiner—Mukund J. Shah
Assistant Examiner—Tamthom N. Truong
(74) Attorney, Agent, or Firm—McDonnell Boehnen Hulbert & Berghoff; Steven J. Sarussi

(57) ABSTRACT

Disclosed are compounds of the formula:

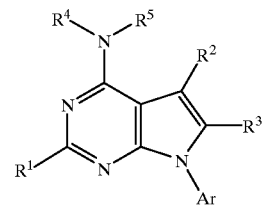

wherein Ar, $R^1$, $R^2$, $R^3$, $R^4$ and $R^5$ are defined herein, which compounds are selective antagonists at CRF1 receptors and are therefore useful in the diagnosis and treatment of stress related disorders such as post traumatic stress disorder (PTSD) as well as depression, headache, anxiety, cardiovascular disorders, and eating disorders. Methods of treatment of such disorders and well as packaged pharmaceutical compositions are also disclosed.

13 Claims, No Drawings

9H-PYRIMIDO [4,5-B] INDOLE DERIVATIVES: CRF1 SPECIFIC LIGANDS

This application claims priority from provisional application No. 60/131,719, filed Apr. 30, 1999, which is incorporated herein by reference in its entirety.

BACKGROUND OF THE INVENTION

1. Field of the Invention

This invention relates to 9H-pyrimido[4,5-b]indole derivatives that modulate cell surface receptors, especially corticotropin-releasing factor 1 (CRF1) receptors. The invention also relates to 9H-pyrimido[4,5-b]indole derivatives that bind selectively to CRF1 receptors. In a further aspect the invention includes pharmaceutical compositions comprising such compounds and the use of such compounds in treatment of psychiatric disorders and neurological diseases, including major depression, anxiety-related disorders, post-traumatic stress disorder (PTSD), supranuclear palsy and feeding disorders, as well as treatment of immunological, cardiovascular or heart-related diseases and colonic hypersensitivity associated with psychopathological disturbance and stress. Additionally this invention relates to the use such compounds as probes for the localization of CRF1 receptors in cells and tissues.

2. Description of the Related Art

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

CRF has also been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist-helical ovine CRF (9-41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15-1788, which was without behavioral activity alone in the operant conflict test, reversed the effects of CRF in a dose-dependent manner, while the benzodiazepine inverse agonist FG 7142 enhanced the actions of CRF.

CRF has also been implicated in the pathogeneisis of certain immunological, cardiovascular or heart-related diseases such as hypertension, tachycardia and congestive heart failure, stroke and osteoporosis, as well as in premature birth, psychosocial dwarfism, stress-induced fever, ulcer, diarrhea, post-operative ileus and colonic hypersensitivity associated with psychopathological disturbance and stress.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders. Of particular interest are that preliminary studies examining the effects of a CRF receptor antagonist peptide (-helical $CRF_{9-41}$) in a variety of behavioral paradigms have demonstrated that the CRF antagonist produces "anxiolytic-like" effects qualitatively similar to the benzodiazepines.

Certain pyrido[2,3-b]indoles and pyrimido[4,5-b]indoles have been described. See, for example, Arzneim.-Forsch. 1978, 28, 1056–65) and Khim. Geterotsikl. Soedin. 1991, 6, 852).

SUMMARY OF THE INVENTION

The invention provides compounds of Formula I (shown below), and pharmaceutical compositions comprising compounds of Formula I. Such compounds bind to cell surface receptors, preferably G-coupled protein receptors, especially CRF receptors and most preferably CRF1 receptors. Preferred compounds of the invention exhibit high affinity for CRF 1 receptors. Additionally, preferred compounds of the invention also exhibit high specificity for CRF1 receptors.

Preferred compounds of the present invention exhibit activity as corticotropin releasing factor receptor antagonists and appear to suppress the anxiogenic effects of CRF hypersecretion. The invention also provides methods of using compounds of Formula I for the suppression of CRF hypersecretion and for the treatment of anxiogenic and stress-related disorders.

The invention further comprises methods of treating patients suffering from certain disorders that are responsive to modulation of CRF1 receptors with an effective amount of a compound of the invention. These disorders include CNS disorders, particularly affective disorders, anxiety disorders, stress-related disorders, including post traumatic stress disorder (PTSD) as well as depression, headache, eating disorders and substance abuse. In another aspect, the invention provides methods for preventing such disorders, which methods comprise administration to a patient an effective amount of a compound of Formula I.

Treatment of human patients suffering from such disorders as well as other animals domesticated companion animals (pets) or livestock animals in encompassed by the invention.

In another aspect, the invention provides pharmaceutical compositions comprising compounds of Formula I or the pharmaceutically acceptable salts or solvates thereof. The invention also includes packaged pharmaceutical compositions of compounds, together with instructions for use.

Additionally this invention relates to the use of the compounds of the invention (particularly labeled compounds of this invention) as probes for the localization of receptors in cells and tissues and as standards and reagents for use in determining the receptor-binding characteristics of test compounds. Labeled compounds of the invention may be used for in vitro studies such as autoradiography of tissue sections or for in vivo methods, e.g. PET or SPECT scanning. Particularly, preferred compounds of the invention are useful as standards and reagents in determining the ability of a potential pharmaceutical to bind to the CRF1 receptor. The invention also provides methods of inhibiting the binding of CRF to CRF receptors and to methods of altering the signal-transducing activity of CRF receptors.

In yet another aspect, the invention provides intermediates useful in the preparation of the compounds of Formula I.

Accordingly, a broad embodiment of the invention is directed to compounds of Formula I:

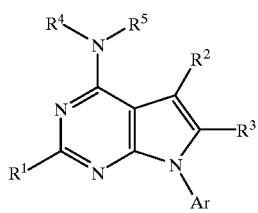

I or pharmaceutically acceptable salts thereof, wherein:
Ar, $R^1$, $R^2$, $R^3$, $R^4$, and $R^5$ are defined below.

DETAILED DESCRIPTION OF THE INVENTION

The invention provides compounds of Formula I:

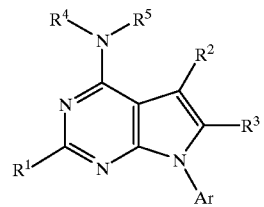

or pharmaceutically acceptable salts thereof, wherein:
Ar is phenyl, 1- or 2-naphthyl, 2-, 3-, or 4-pyridyl, 2-, 4- or 5-pyrimidinyl, each of which is mono-, di-, or trisubstituted with halogen, trifluoromethyl, hydroxy, amino, cyano, carboxamide, $C_1$–$C_6$ alkyl, $C_1$–$C_6$ alkoxy, $C_3$–$C_7$ cycloalkyl, or amino($C_1$–$C_6$)alkyl with the proviso that at least one of the ortho or para positions of Ar is substituted;
$R^1$ is hydrogen, halogen, trifluoromethyl, carboxamide, carboxylate, $C_1$–$C_6$ alkyl, $C_3$–$C_7$ cycloalkyl, or ($C_1$–$C_6$ alkyl)-$G^1$—$R^6$ wherein $G^1$ is nitrogen, oxygen or sulfur and $R^6$ is hydrogen, $C_3$–$C_7$ cycloalkyl, or $C_1$–$C_6$ alkyl;
$R^2$ and $R^3$ together represent —($C_0$–$C_2$)—$G^2$—($C_2$–$C_4$)— wherein $G^2$ is methylene, oxygen, sulfur or $NR^7$, wherein $R^7$ is hydrogen, $C_3$–$C_7$ cycloalkyl, or $C_1$–$C_6$ alkyl; or
$R^2$ and $R^3$ taken together represent —CH=A—CH=CH— wherein A is N or $CR^8$;

$R^8$ is —($C_0$–$C_6$ alkyl)—Z; where
Z is —$CR^9R^{9'}$, $NR^9R^{9'}$, $OR^9$ or $SR^9$; and
$R^9$ and $R^{9'}$ independently represent hydrogen or ($C_1$–$C_6$) alkyl;
$R^4$ and $R^5$ are the same or different and represent hydrogen, hydroxy, $C_1$–$C_6$ alkoxy($C_1$–$C_6$)alkyl, hydroxy($C_1$–$C_6$) alkyl, $C_3$–$C_7$ cycloalkyl, or $C_1$–$C_6$ alkyl; or
phenyl, 2-, 3-, or 4-pyridyl, 2- or 3-thienyl, or 2-, 4-, or 5-pyrimidinyl, each of which is optionally mono- or disubstituted with halogen, trifluoromethyl, hydroxy, $C_1$–$C_6$ alkyl, $C_3$–$C_7$ cycloalkyl, or $C_1$–$C_6$ alkoxy; or
$R^4$ and $R^5$ together represent —($C_2$–$C_3$)—$G^3$—($C_1$–$C_3$)— where
$G^3$ is methylene, 1,2-phenylene, oxygen, sulfur or $NR^{10}$; and
$R^{10}$ is $C_1$–$C_6$ alkyl, $C_3$–$C_7$ cycloalkyl, phenyl, 2-, 3-, or 4-pyridyl, 2- or 3-thienyl, or 2-, 4- or 5-pyrimidyl.

Preferred compounds of Formula I include those where Ar is phenyl mono-, di-, or trisubstituted with halogen, trifluoromethyl, hydroxy, amino, cyano, carboxamide, $C_1$–$C_6$ alkyl, $C_1$–$C_6$ alkoxy, $C_3$–$C_7$ cycloalkyl, or amino ($C_1$–$C_6$)alkyl with the proviso that at least one of the ortho positions of Ar is substituted. Other preferred compounds of Formula I are those where $R_1$ is lower alkyl, more preferably $C_1$–$C_3$ alkyl, and most preferably methyl. More preferred compounds of Formula I include those where Ar is phenyl substituted in the 2 and 4 positions with methyl, fluoro or chloro, or phenyl trisubstituted in the 2, 4, and 6-positions with $C_1$–$C_2$ alkyl, more preferably methyl. Other preferred compounds of Formula I are those where $R^4$ and $R^5$ independently represent hydrogen, $C_1$–$C_6$ alkoxy($C_1$–$C_6$)alkyl, $C_3$–$C_7$ cycloalkyl, or $C_1$–$C_6$ alkyl. Still other preferred compounds of the invention are those where $R_2$ is $C_1$–$C_2$ alkyl, $C_1$–$C_2$ alkyl carboxylate, or amino ($C_1$–$C_2$)alkyl.

A preferred group of compounds of Formula I are those wherein $R_2$ and $R_3$ together represent —CH=$CR^8$—CH=CH—. Such compounds are represented by Formula II:

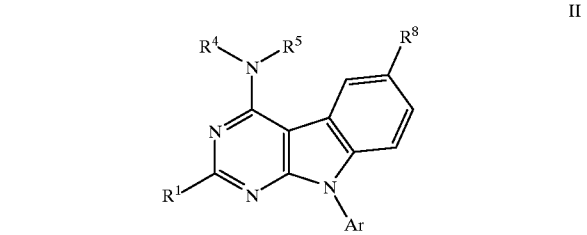

II where the substituents are defined as for Formula I.

Preferred compounds of Formula II are those where wherein $R^8$ is hydrogen or $C_1$–$C_6$ alkyl. Such compounds are hereinafter referred to as compounds of Formula II-A. Preferred compounds of Formula II-A include those where Ar is phenyl substituted in the 2 and 4 positions with methyl, fluoro or chloro or Ar is 2,4,6-trimethylphenyl. Other preferred compounds of Formula II-A are those where $R_1$ is lower alkyl, more preferably $C_1$–$C_3$ alkyl, and most preferably methyl. More preferably, compounds of Formula II-A are those where Ar is 2,4,6-trimethylphenyl and $R_1$ is lower alkyl, more preferably $C_1$–$C_3$ alkyl, and most preferably methyl.

Particularly preferred compounds of Formula II-A include those where $R^8$ is hydrogen or $C_1$–$C_6$ alkyl, Ar is 2,4,6-trimethylphenyl; and $R^4$ and $R^5$ independently represent hydrogen, $C_1$–$C_6$ alkoxy($C_1$–$C_6$)alkyl, $C_3$–$C_7$ cycloalkyl, or $C_1$–$C_6$ alkyl.

Other preferred compounds of Formula II are those where $R^8$ is —($C_0$–$C_6$ alkyl)-$OR^9$ or —($C_0$–$C_6$ alkyl)-$NR^9R^{9'}$; and $R^9$ and $R^{9'}$ are independently hydrogen or ($C_1$–$C_6$)alkyl. Such compounds are designated as compounds of Formula II-B herein. More preferred are compounds of II-B are where $R^8$ is —$NR^9R^{9'}$. Particularly preferred compounds of II-B are those where at least one of $R^9$ and $R^{9'}$ is $C_1$–$C_6$ alkyl, preferably methyl, ethyl, or propyl. The most preferred compounds of II-B are those where Ar is 2,4,6-trimethylphenyl. Other most preferred compounds of Formula II-B are those where $R^4$ and $R^5$ independently represent hydrogen, $C_1$–$C_6$ alkoxy($C_1$–$C_6$)alkyl, $C_3$–$C_7$ cycloalkyl, or $C_1$–$C_6$ alkyl.

Other preferred compounds of Formula II-B are those where $R_1$ is lower alkyl, more preferably $C_1$–$C_3$ alkyl, and most preferably methyl. More preferably, compounds of Formula II-B are those where Ar is 2,4,6-trimethylphenyl and $R_1$ is lower alkyl, more preferably $C_1$–$C_3$ alkyl, and most preferably methyl.

Other preferred compounds of Formula I are those where $R^2$ and $R^3$ together represent —($C_0$–$C_2$)$CH_2$($C_2$–$C_4$)—. Such compounds are represented by Formula III.

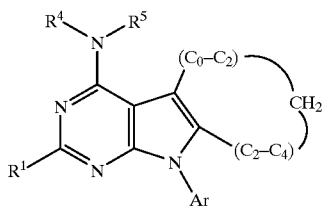

III

Preferred compounds of Formula III are those where —($C_0$–$C_2$)$CH_2$($C_2$–$C_4$)— and the carbon atoms at the 5 and 6 positions of the pyrrolo[2,3-d]pyrimidine form a five- or six-membered ring. Examples of such compounds have the following general formulas:

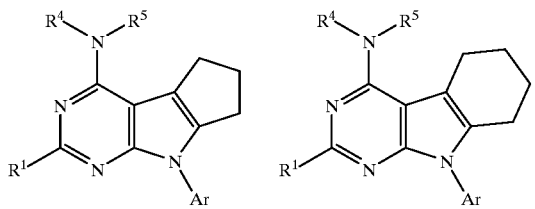

Since $C_2$, $C_3$, and $C_4$ include branched alkylene groups, the compounds of these formulas may be substituted on the unsaturated ring (i.e., the non-nitrogen-containing ring) with $C_1$–$C_6$ alkyl within the definition of —($C_0$–$C_2$)$CH_2$ ($C_2$–$C_4$)—. Preferred compounds of Formula III include those wherein Ar is 2,4,6-trimethylphenyl. Particularly preferred compounds of Formula III are those where $R^4$ and $R^5$ independently represent hydrogen, $C_1$–$C_6$ alkoxy($C_1$–$C_6$) alkyl, $C_3$–$C_7$ cycloalkyl, or $C_1$–$C_6$ alkyl.

Other preferred compounds of Formula III are those where $R_1$ is lower alkyl, more preferably $C_1$–$C_3$ alkyl, and most preferably methyl. More preferably, compounds of Formula III are those where Ar is 2,4,6-trimethylphenyl and $R_1$ is lower alkyl, more preferably $C_1$–$C_3$ alkyl, and most preferably methyl. Particularly preferred compounds of Formula III are those where Ar is 2,4,6-trimethylphenyl, $R_1$ is lower alkyl, preferably methyl, and $R^4$ and $R^5$ independently represent hydrogen, $C_1$–$C_6$ alkoxy($C_1$–$C_6$)alkyl, $C_3$–$C_7$ cycloalkyl, or $C_1$–$C_6$ alkyl.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table 1 and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "$C_1$–$C_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, and butyl.

Preferred $C_3$–$C_7$ cycloalkyl groups herein are cyclopropyl and cyclopropylmethyl.

By "$C_1$–$C_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

As used herein, $C_0$ represents a bond.

When the terms $C_1$, $C_2$, $C_3$, and $C_4$ are used the context of a "$C_0$–$C_2$", "$C_1$–$C_3$", "$C_1$–$C_3$", or "$C_2$–$C_4$" group, the terms represent alkylene groups having 1, 2, 3, or 4 carbon atoms respectively. The alkylene groups may be straight or branched chain groups. For example, $C_3$ includes groups of the formulas:

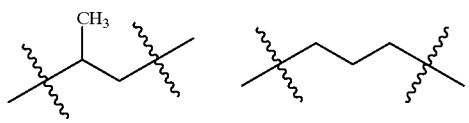

Examples of C$_4$ groups are:

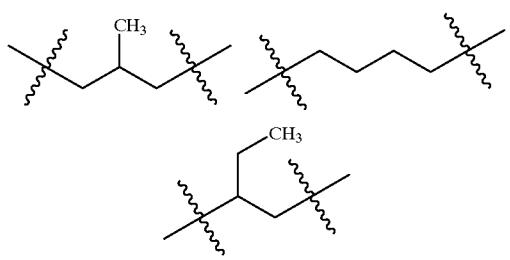

Examples of compounds of the invention where R$^2$ and R$^3$ together represent groups of the formula —(C$_0$–C$_2$)—G$^2$—(C$_2$–C$_4$)— include the following:

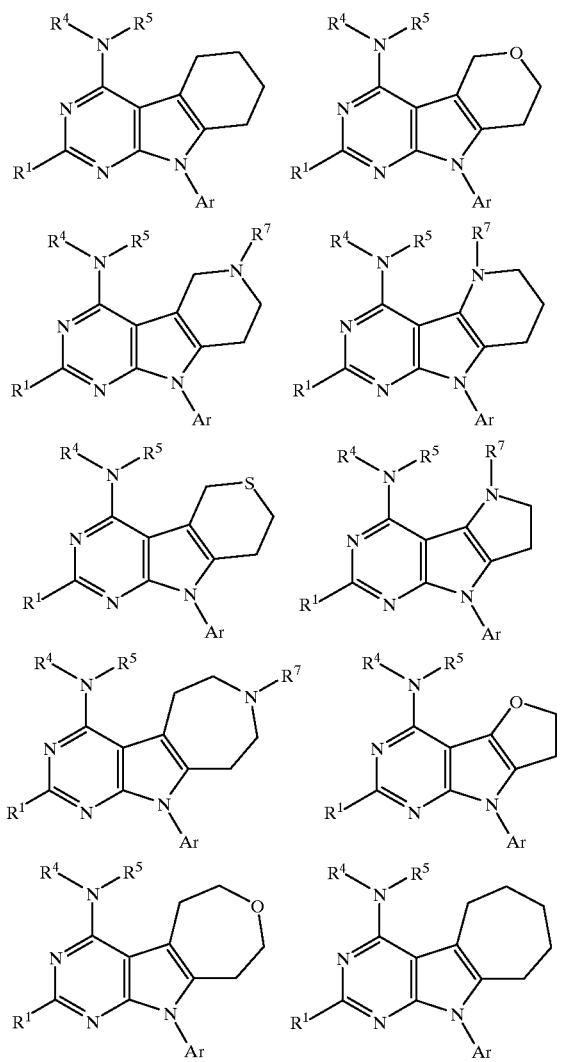

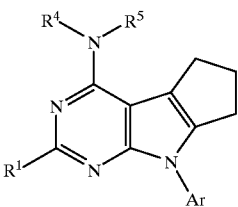

The alkylene groups in the —(C$_0$–C$_2$)—G$^2$—(C$_2$–C$_4$)— group, i.e., "C$_1$", "C$_2$", "C$_3$", and "C$_4$", groups, may, provided there is a sufficient number of carbon atoms, be straight or branched chain alkyl groups. Thus, the invention encompasses compounds having the following general structures:

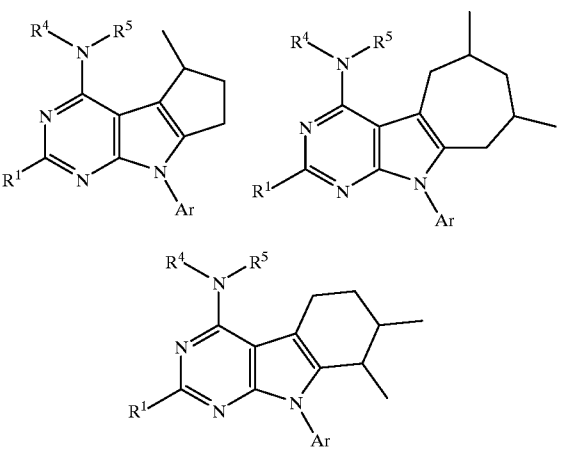

Representative compounds of the invention are shown in Table 1.

TABLE 1

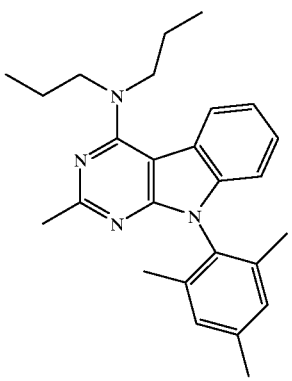

1

TABLE 1-continued

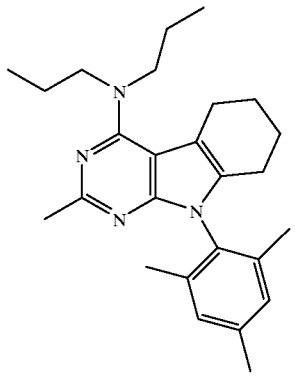

2

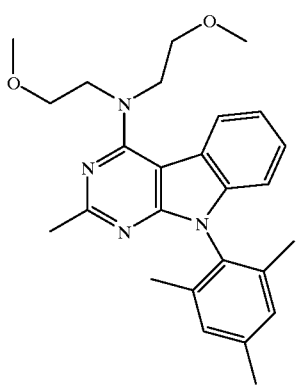

3

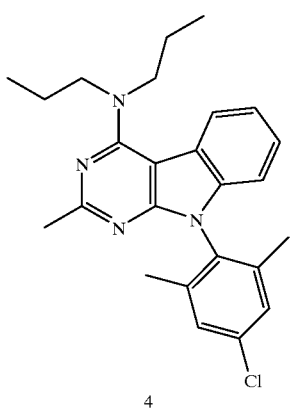

4

TABLE 1-continued

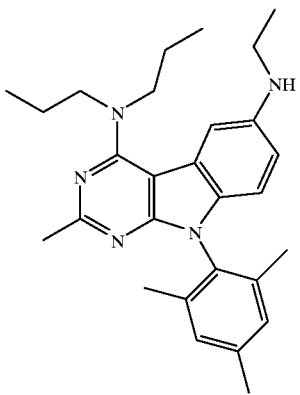

5

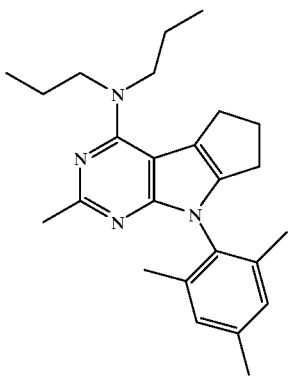

6

The present invention also encompasses methods for inhibiting the binding of CRF to the CRF1 receptor which methods involve contacting a compound of the invention with cells expressing CRF1 receptors, wherein the compound is present at a concentration sufficient to inhibit CRF binding to cells expressing CRF1 receptors in vitro. These methods include inhibiting the binding of CRF to CRF1 receptors in vivo, e.g., in a patient using an amount of a compound of Formula I that would be sufficient to inhibit the binding of CRF to CRF1 receptors in vitro. The cells expressing CRF1 receptors in vitro may either naturally express CRF1 receptors, e.g. IMR32 cells, or may recombinantly express cloned CRF1 receptors. The amount of a compound that would be sufficient to inhibit the binding of CRF to the CRF1 receptor may be readily determined via CRF1 receptor binding assays, such as the assay described in Example 6.

The present invention also pertains to methods for altering the signal-transducing activity of CRF1 receptors, said method comprising exposing cells expressing such receptors to an effective amount of a compound of the invention. These methods include altering the signal-transducing activity of CRF1 receptors in vivo, e.g., in a patient using an amount of a compound of Formula I that would be sufficient to alter the signal-transducing activity of CRF1 receptors in vitro. The amount of a compound that would be sufficient to alter the signal-transducing activity of CRF1 receptors may be determined via an CRF1 receptor signal transduction assay, such as the assay described in Example 7.

The compounds of the invention and labeled derivatives thereof are also useful as standards and reagents in determining the ability of a potential pharmaceutical to bind to the CRF1 receptor.

Labeled derivatives of the compounds provided by this invention are also useful as radiotracers for positron emission tomography (PET) imaging or for single photon emission computerized tomography (SPECT).

The invention also pertains to the use of compounds of general Formula I in the treatment of various stress-related disorders. The interaction of compounds of the invention with CRF receptors is shown in the examples.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or stress disorders a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to CRF1 receptor modulation, e.g., treatment of anxiety, depression, PTSD, cardiovascular disorder, headache and eating disorders by CRF1 receptor modulation.

The packaged pharmaceutical compositions include a container holding a therapeutically effective amount of at least one CRF1 receptor modulator as described supra and instructions (e.g., labeling) indicating the contained CRF1 receptor ligand is to be used for treating a disorder responsive to CRF1 receptor modulation in the patient.

Representative suitable synthetic routes for the preparation of compounds of the invention are given in Schemes I and II. Those having skill in the will recognize that the starting materials, solvents, and reaction conditions may be varied and additional steps employed to produce compounds encompassed by the present invention.

Scheme I

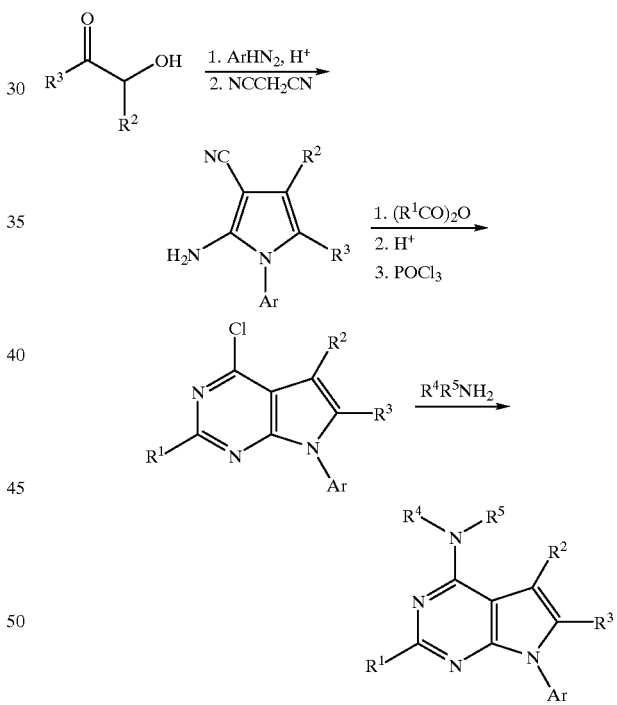

The substituents Ar, $R^1$, $R^2$, $R^3$, $R^4$ and $R^5$ are as defined above for Formula I.

Scheme II

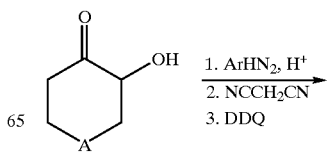

-continued

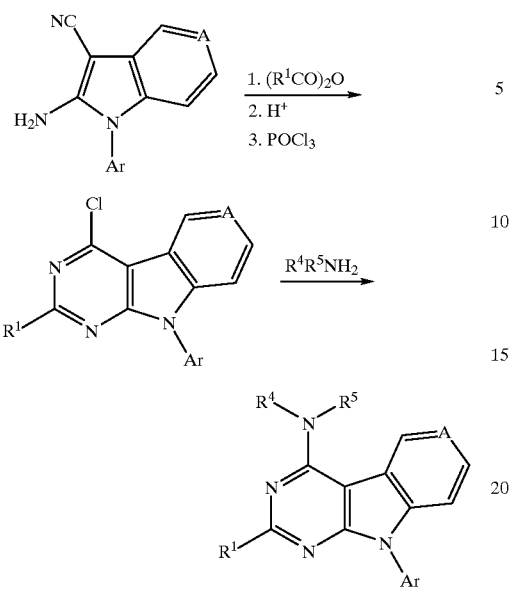

The definitions for the substituents A, Ar, $R^1$, $R^2$, $R^3$, $R^4$ and $R^5$ are set forth above for Formula I.

Compounds of the invention where $R^2$ and $R^3$ together represent —$(C_0$–$C_2)$—$G^2$—$(C_2$–$C_4)$— may be prepared by avoiding the aromatization portion (treatment with DDQ, 2,3-dichloro-5,6-dicyano-1,4-benzoquinone) of the synthesis set forth in Scheme II.

The preparation of the compounds of the present invention is illustrated further by the following examples, which are not to be construed as limiting the invention in scope or spirit to the specific procedures and compounds described in them.

The disclosures in this application of all articles and references, including patents, are incorporated herein by reference.

Commercial reagents were used without further purification. THF refers to tetrahydrofuran. LDA refers to lithium diisopropylamide. Room or ambient temperature refers to about 20 to about 25° C. Concentration means removal of solvent under reduced pressure, e.g., by the use of a rotary evaporator. Mass spectral data were obtained either by CI or APCI methods.

The following compounds are prepared essentially according to the procedures set forth in Example 1, without the aromatization procedure of Example 1B.

EXAMPLE 1

A. 2-Amino-4,5,6,7-tetrahydro-1-phenyl-1H-indole-3-carbonitrile

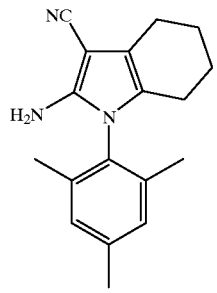

A mixture of 2,4,6-trimethylaniline (500 g) and adipoin (2-hydroxycyclohexanone, 464 g) in toluene (2.5 L) is heated to reflux. A theoretical amount of water is removed azeotropically over the course of 3 hours. The mixture is cooled to ambient temperature, then malononitrile (244 g) and ammonium acetate (57 g) are added. The reaction is slowly reheated back to reflux for about 1 hour with azeotropic removal of water. After cooling, the precipitate that forms overnight is collected by filtration. The dark solid is washed with ethanol and dried to afford 540 g of a white powder: MS 280 (M+H).

B. 2-Amino-1-phenyl-1H-indole-3-carbonitrile

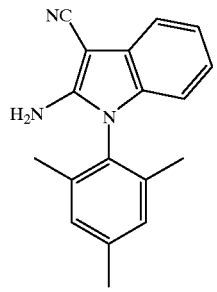

Compound from Example 1A (20 g) is dissolved in 1,4-dioxane (300 mL) and added DDQ (34 g) portionwise to the solution. The reaction is stirred for 1 hour then filtered through celite to remove insoluble side products. The filtrate is concentrated and allowed to solidify. The product is collected by filtration and washed with ethanol to yield 16 g of a tan colored powder: MS 276 (M+H).

C. 4-Hydroxy-2-methyl-9-(2,4,6-trimethylphenyl)-9H-pyrimidino[4,5-b]indole

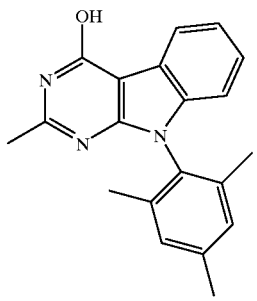

A mixture of compound from Example 1B (30 g), acetic anhydride (15 mL) and acetic acid (30 mL) is refluxed for 1 hour then concentrated to a solid. Phosphoric acid (40 mL, 85%) is added to the amide. The mixture is then refluxed for 0.5 hours and cooled to ambient temperature. The solution is poured onto ice and the precipitate that forms is collected by filtration. The solids are then washed with water and ethanol: MS 318 (M+H).

D. 4-Chloro-2-methyl-9-(2,4,6-trimethylphenyl)-9H-pyrimidino[4,5-b]indole

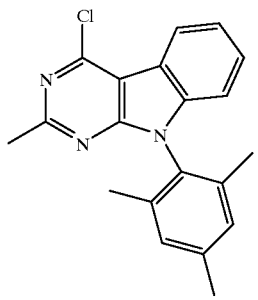

A sample of the compound from Example 1B (2.2 g) is refluxed in phosphoryl chloride (30 mL) for 3 hours. The excess phosphoryl chloride is removed under reduced pressure and the residue partitioned between aqueous potassium carbonate and dichloromethane. The aqueous layer is extracted with a second portion of dichloromethane. The combined extracts are then dried over sodium sulfate, filtered and concentrated to give a tan colored solid: MS 336 (M+H).

E. 4-(N,N-Dipropyl)amino-2-methyl-9-(2,4,6-trimethylphenyl)-9H-pyrimidino[4,5-b]indole (Compound 1)

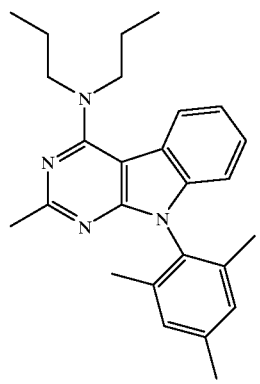

A mixture containing a sample of the compound prepared as set forth above in Example 1D (1.0 g) and dipropylamine (1.0 mL) in N-methylpyrrolidinone (5 mL) is heated to 100° C. for 2 hours. The mixture is diluted with ethyl acetate and washed with water, aqueous ammonium chloride, aqueous sodium bicarbonate, and brine. The mixture is then dried over sodium sulfate, filtered and concentrated. Purificarbon by flash chromatography using 10% ethyl acetate in hexanes as eluant affords the title compound: MS 401 (M+H).

The following compounds are prepared essentially according to the procedures set forth above in Example 1.

EXAMPLE 2 a) 4-(N-Cyclopropylmethyl-N-propyl)amino-2-methyl-9-(2,4,6-trimethylphenyl)-9H-pyrimidino[4,5-b]indole: MS 413 (M+H).

b) 4-(N,N-Dipropyl)amino-2-methyl-9-(4-bromo-2,6-dimethylphenyl)-9H-pyrimidino[4,5-b]indole: MS 465 (M+H).

c) 4-(N,N-Dipropyl)amino-2-methyl-9-(2,6-dimethylphenyl)-9H-pyrimidino[4,5-b]indole: MS 387 (M+H).

d) 4-Bis(2-methoxyethyl)amino-2-methyl-9-(4-bromo-2,6-dimethylphenyl)-9H-pyrimidino[4,5-b]indole: MS 497 (M+H).

e) 4-(N,N-Dipropyl)amino-2-methyl-9-(4-chloro-2-methylphenyl)-9H-pyrimidino[4,5-b]indole: MS 407 (M+H).

f) 4-(N,N-Dipropyl)amino-2-methyl-9-(4-cyano-2,6-dimethylphenyl)-9H-pyrimidino[4,5-b]indole: MS 412 (M+H).

g) 4-(N,N-Dipropyl)amino-2-methyl-9-(4-aminomethyl-2,6-dimethylphenyl)-9H-pyrimidino[4,5-b]indole: MS 416 (M+H).

h) 4-(N,N-Dipropyl)amino-2-methyl-9-(2,6-dimethyl-4-(methylaminomethyl)phenyl)-9H-pyrimidino[4,5-b]indole: MS 430 (M+H).

i) 4-Bis(2-methoxyethyl)amino-2-methyl-9-(2,4,6-trimethylphenyl)-9H-pyrimidino[4,5-b]indole: MS 433 (M+H) (Compound 3).

j) 4-(N-(2-Hydroxyethyl)-N-Cyclopropylmethyl)amino-2-methyl-9-(2,4,6-trimethylphenyl)-9H-pyrimidino[4,5-b]indole: MS 415 (M+H).
k) 4-(N-(2-Hydroxyethyl)-N-Cyclopropyl)amino-2-methyl-9-(2,4,6-trimethylphenyl)-9H-pyrimidino[4,5-b]indole: MS 401 (M+H).
l) 4-(N-Cyclopropylmethylamino)-2-methyl-9-(2,4,6-trimethylphenyl)-9H-pyrimidino[4,5-b]indole: MS 371 (M+H).

EXAMPLE 3

The following compounds are prepared essentially according to the procedures set forth in Example 1 but without the aromatization procedure of Example 1B.

a) 4-(N-Cyclopropylmethyl-N-propyl)amino-9-(2,4,6-trimethylphenyl)-5,6,7,8-tetrahydro-9H-pyrimidino[4,5-b]indole: MS 403 (M+H).
b) 4-(N,N-Dipropyl)amino-9-(2,4,6-trimethylphenyl)-5,6,7,8-tetrahydro-9H-pyrimidino[4,5-b]indole: MS 391 (M+H) (Compound 2).
c) 4-(N-Cyclopropylmethyl-N-propyl)amino-2-methyl-9-(2,4,6-trimethylphenyl)-5,6,7,8-tetrahydro-9H-pyrimidino[4,5b]indole: MS 417 (M+H).
d) 4-(N,N-Dipropyl)amino-2-methyl-9-(2,4,6-trimethylphenyl)-5,6,7,8-tetrahydro-9H-pyrimidino[4,5-b]indole: MS 405 (M+H).
e) 4-(N-Propyl-N-methyl)amino-2-methyl-9-(2,4,6-trimethylphenyl)-5,6,7,8-tetrahydro-9H-pyrimidino[4,5-b]indole: MS 377 (M+H).
f) 4-(N-Butyl-N-methyl)amino-9-(2,4,6-trimethylphenyl)-5,6,7,8-tetrahydro-9H-pyrimidino[4,5-b]indole: MS 377 (M+H).
g) 4-(N-Propyl)amino-8-(2,4,6-trimethylphenyl)-5,6,7-trihydrocyclopenta[2,1-d]-8H-pyrimidino[4,5-b]indole: MS 335 (M+H).
h) 4-(N,N-Dipropyl)amino-2-methyl-8-(2,4,6-trimethylphenyl)-5,6,7-trihydrocyclopenta[2,1-d]-8H-pyrimidino[4,5-b]indole: MS 391 (M+H) (Compound 6).
i) 4-Bis(2-methoxyethyl)amino-2-methyl-9-(2,4,6-trimethylphenyl)-5,6,7,8-tetrahydro-9H-pyrimidino[4,5-b]indole: MS 437 (M+H).
j) Ethyl 4-(dipropylamino)-9-(2,4,6-trimethylphenyl)-5,6,7,8-tetrahydropyrimidino[4,5-b]indole-2-carboxylate: MS 463 (M+H).
k) 4-(N,N-Dipropyl)amino-2-carboxyamido-9-(2,4,6-trimethylphenyl)-5,6,7,8-tetrahydro-9H-pyrimidino[4,5-b]indole: MS 434 (M+H).
l) 4-(N,N-Dipropyl)amino-2-aminomethyl-9-(2,4,6-trimethylphenyl)-5,6,7,8-tetrahydro-9H-pyrimidino[4,5-b]indole: MS 420 (M+H).
m) 4-(N,N-Dipropyl)amino-8-(2,4,6-trimethylphenyl)-5,6,7-trihydrocyclopenta[2,1-d]-8H-pyrimidino[4,5-b]indole: MS 377 (M+H).
n) 4-(N,N-Dibutylamino)-2-methyl-9-(2,4,6-trimethylphenyl)-5,6,7,8-tetrahydro-9H-pyrimidino[4,5-b]indole: MS 433 (M+H).
o) 4-(N,N-Dibutylamino)-2-methyl-9-(2,4,6-trimethylphenyl)-5,6,7,8-tetrahydro-9H-pyrimidino[4,5-b]indole: MS 419 (M+H).
p) 4-(N-(2-(4-Chlorophenyl)ethyl)amino)-2-methyl-9-(2,4,6-trimethylphenyl)-5,6,7,8-tetrahydro-9H-pyrimidino[4,5-b]indole: MS 459 (M+H).
q) 4-(N-(2-(4-Chlorophenyl)ethyl)amino)-2-methyl-9-(2,4-dimethylphenyl)-5,6,7,8-tetrahydro-9H-pyrimidino[4,5-b]indole: MS 445 (M+H).
r) 4-(N-(4-Chlorophenyl)methylamino)-2-methyl-9-(2,4,6-trimethylphenyl)-5,6,7,8-tetrahydro-9H-pyrimidino[4,5-b]indole: MS 445 (M+H).
s) 4-(N-(2-Methylphenyl)methylamino)-2-methyl-9-(2,4,6-trimethylphenyl)-5,6,7,8-tetrahydro-9H-pyrimidino[4,5-b]indole: MS 425 (M+H).
t) 4-(N-(3-Trifluromethylphenyl)methylamino)-2-methyl-9-(2,4,6-trimethylphenyl)-5,6,7,8-tetrahydro-9H-pyrimidino[4,5-b]indole: MS 479 (M+H).
u) 4-(N-Propyl-N-methyl)amino-2-methyl-9-(2,4,6-trimethylphenyl)-5,6,7,8-tetrahydro-9H-pyrimidino[4,5-b]indole.

EXAMPLE 4

4-(N,N-Dipropyl)amino-6-ethylamino-2-methyl-9-(2,4,6-trimethylphenyl)-9H-pyrimidino[4,5-b]indole (Compound 5)

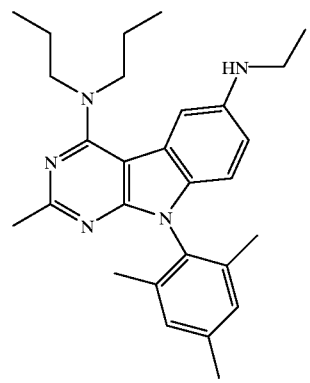

A sample of the compound prepared in Example 1C (1.0 g) is dissolved in a 30:1 mixture of acetic acid and 70% nitric acid (35 mL). The resulting solution is refuxed for 1.5 hours, cooled and poured into cold water after which the solids are collected by filtration and dried. The subsequent chlorination and substitution reactions with phoshorous oxychloride and dipropylamine, respectively are carried out according to Examples 1-D and 1-E. The nitro functionality is then reduced by hydrogenation at 50 psi in a solution of methanol (20 mL) containing 10% palladium on carbon (0.5 g). After 6 hours the solution is filtered and concentrated. Next, the aniline product is acylated by refluxing in acetic acid (15 mL) for 6 hours. The solution is concentrated and extracted from aqueous sodium carbonate solution with dichloromethane. The extract is then dried over sodium sulfate, filtered and concentrated. The resulting amide is dissolved in tetrahydrofuran (15 mL) and treated with borane-methylsulfide complex (0.6 mL). The solution is refluxed for 3 hours, quenched with a large excess of methanol (20 mL) and concentrated. The final product is purified by flash chromatography using 10% ethyl acetate in hexanes as eluant: MS 444 (M+H).

EXAMPLE 5

The following compounds are prepared essentially according to the procedures set forth above in Example 4.

a) 4-(N,N-Dipropyl)amino-6-diethylamino-2-methyl-9-(2,4,6-trimethylphenyl)-9H-pyrimidino[4,5-b]indole: MS 472 (M+H).
b) 4-(N-Cyclopropylmethyl-N-propyl)amino-6-ethylamino-2-methyl-9-(2,4,6-trimethylphenyl)-9H-pyrimidino[4,5-b]indole: MS 456 (M+H).
c) 4-(N,N-dipropylamino)-2-methyl-6dimethylamino-9-(2,4,6-trimethylphenyl)-9H-pyrimidino[4,5-b]indole: MS 444 (M+H).

The following two assays for human CRF1 receptor activity are standard assays of CRF binding that may be used to determine the affinity of CRF for the CRF receptor. The second assay, described in Example 7 is also a CRF1 signal transduction assay.

EXAMPLE 6
Assay for Recombinant Human $CRF_1$ Receptor Binding Activity

CRF receptor binding is performed using a modified version of the assay described by Grigoriadis and De Souza (*Methods in Neurosciences,* Vol. 5, 1991). Membrane pellets containing CRF receptors are re-suspended in 50 mM Tris buffer pH 7.7 containing 10 mM $MgCl_2$ and 2 mM EDTA and centrifuged for 10 minutes at 48000 g. Membranes are washed again and brought to a final concentration of 1500 mg/ml in binding buffer (Tris buffer above with 0.1 % BSA, 15 mM bacitracin and 0.01 mg/mL aprotinin). For the binding assay, 100 mL of the membrane preparation is added to 96 well microtube plates containing 100 mL of $^{125}$I-CRF (SA 2200 Ci/mmol, final concentration of 100 pM) and 50 mL of drug. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass.). The binding affinity for the compounds of Formula I expressed as $IC_{50}$ value, generally ranges from about 0.5 nanomolar to about 10 micromolar.

Preferred compounds of the invention exhibit good activity in standard in vitro receptor binding assays, specifically the assay set forth in Example 7 below. Particularly preferred compounds of the invention have an $IC_{50}$ of about 10 micromolar or less, still more preferably an $IC_{50}$ of about 100 nanomolar or less, even more preferably an $IC_{50}$ of about 10 nanomolar or less, or even 1 nanomolar or less in such a defined standard in vitro CRF receptor binding assay.

EXAMPLE 7
Assay for Human CRF Receptor Binding Activity in IMR32 Cells

Alternatively, the binding activity of the compounds of formula I to the human $CRF_1$ receptor can be measured as follows:

IMR-32 human neuroblastoma cells are grown to 80% confluence in EMEM containing Earle's Balanced Salts and 2 mM l-glutamine with 10% FBS, 25 mM HEPES, 1 mM Sodium Pyruvate, and nonessential amino acids. At this time, flasks of cells are treated with 2.5 uM 5-bromo-2'-deoxyuridine (Br-dU) for 10 days. Media is changed every 3–4 days across the 10-day period. Cells are harvested using No-Zyme (JRH Biosciences) and rinsed with PBS. For membrane preparation, cells are homogenized in wash buffer (50 mM Tris HCl, 10 mM $MgCl_2$, 2 mM EGTA, pH 7.4) and centrifuged at 48,000×g for 10 minutes at 4° C. Pellets are resuspended, homogenized and centrifuged two additional times. The receptor binding assay is performed using assay buffer (50 mM Tris HCl, 10 mM $MgCl_2$, 2 mM EGTA, pH 7.4, 0.1% BSA, 0.1 mM bacitracin (22.0 mg/100 mL)), 150 ug protein/tube, and [$^{125}$I]Sauvagine (NEN; 100 pM for competition analysis and 10 pM-1 nM for saturation analysis) to yield a final volume of 200 µL. Nonspecific binding is defined using 2 µM r/h CRF or 9-41 alpha-helical CRF. Cells are incubated for 2 hours at room temperature. The assay is terminated by rapid vacuum filtration (Tomtec: Deepwell 3) through GFC filters presoaked in 1% PEI using ice-cold 50 mM Tris Hcl and dry thoroughly by air. Specific Binding. 70–80%; Kd (nM): 0.30 nM; Bmax (fmole/mg protein): 40–50. $IC_{50}$ values are calculated with the non-linear curve fitting program RS/1 (BBN Software Products Corp., Cambridge, Mass.).

EXAMPLE 8
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 9
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

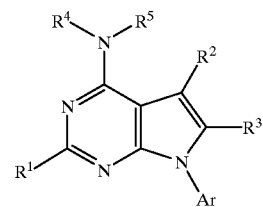

or a pharmaceutically acceptable salt thereof wherein

Ar is phenyl, 1- or 2-naphthyl, 2-, 3-, or 4-pyridyl, 2-, 4- or 5-pyrimidinyl, each of which is mono-, di-, or trisubstituted with halogen, trifluoromethyl, hydroxy, amino, cyano, carboxamide, $C_1$–$C_6$ alkyl, $C_1$–$C_6$ alkoxy, $C_3$–$C_7$ cycloalkyl, or amino($C_1$–$C_6$)alkyl with the proviso that at least one of the ortho or para positions of Ar is substituted;

$R^1$ is hydrogen, halogen, trifluoromethyl, carboxamide, carboxylate, $C_1$–$C_6$ alkyl, $C_3$–$C_7$ cycloalkyl, or ($C_1$–$C_6$ alkyl)-$G^1$—$R^6$ wherein $G^1$ is nitrogen, oxygen or sulfur and $R^6$ is hydrogen, $C_3$–$C_7$ cycloalkyl, or $C_1$–$C_6$ alkyl;

$R^2$ and $R^3$ are taken together, and represent —CH=A—CH=CH—, wherein

A is $CR^8$;

$R^8$ is —$NR^9R^{9'}$; and $R^9$ and $R^{9'}$ independently represent hydrogen or ($C_1$–$C_6$) alkyl;

$R^4$ and $R^5$ are the same or different and represent hydrogen hydroxy, $C_1$–$C_6$ alkoxy($C_1$–$C_6$)alkyl, hydroxy($C_1$–$C_6$) alkyl, $C_3$–$C_7$ cycloalkyl, or $C_1$–$C_6$ alkyl; or phenyl, 2-, 3-, or 4-pyridyl, 2- or 3-thienyl, or 2-, 4-, or 5-pyrimidinyl, each of which is optionally mono- or disubstituted with halogen, hydroxy, $C_1$–$C_6$ alkyl, $C_3$–$C_7$ cycloalkyl, or $C_1$–$C_6$ alkoxy; or $R^4$ and $R^5$ together represent —($C_2$–$C_3$)—$G^3$—($C_1$–$C_3$)— where $G^3$ is methylene, 1,2 phenylene, oxygen, sulfur or $NR^{10}$; and $R^{10}$ is $C_1$–$C_6$ alkyl, $C_3$–$C_7$ cycloalkyl, phenyl, 2-, 3-, or 4-pyridyl, 2- or 3-thienyl, or 2-, 4- or 5-pyrimidyl.

2. A compound according to claim 1, wherein $R^4$ and $R^5$ independently represent hydrogen, $C_1$–$C_6$ alkoxy($C_1$–$C_6$) alkyl, $C_3$–$C_7$ cycloalkyl, or $C_1$–$C_6$ alkyl.

3. A compound according to claim 1, wherein Ar is 2,4,6-trimethylphenyl.

4. A compound according to claim 1 which is 4-(N,N-Dipropyl)amino-6-ethylamino-2-methyl-9-(2,4,6-trimethylphenyl)-9H-pyrimidino[4,5-b]indole.

5. A compound according to claim 1 which is 4-(N,N-Dipropyl)amino-6-diethylamino-2-methyl-9-(2,4,6-trimethylphenyl)-9H-pyrimidino[4,5-b]indole.

6. A compound according to claim 1 which is 4-(N-Cyclopropylmethyl-N-propyl)amino-6-ethylamino-2-methyl-9-(2,4,6-trimethylphenyl)-9H-pyrimidino[4,5-b]indole.

7. A compound according to claim 1 which is (N,N-Dipropylamino)-2-methyl-6-dimethylamino-9-(2,4,6-trimethylphenyl)-9H-pyrimidino[4,5-b]indole.

8. A pharmaceutical composition comprising a compound according to claim 1 and at least one pharmaceutically acceptable carrier or excipient.

9. A method for treating stress, posttraumatic stress disorder, anxiety or depression which comprises administering an effective amount of a compound according to claim 1 to a patient in need thereof.

10. A method for treating obesity or eating disorders which comprises administering an effective amount of a compound according to claim 1 to a patient in need thereof.

11. A compound of the formula:

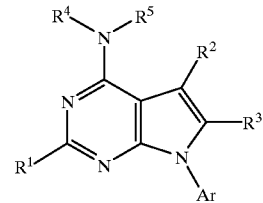

or a pharmaceutically acceptable salt thereof wherein

Ar is phenyl, 1- or 2-naphthyl, 2-, 3-, or 4-pyridyl, 2-, 4- or 5-pyrimidinyl, each of which is mono-, di-, or trisubstituted with halogen, trifluoromethyl, hydroxy, amino, cyano, carboxamide, $C_1$–$C_6$ alkyl, $C_1$–$C_6$ alkoxy, $C_3$–$C_7$ cycloalkyl, or amino($C_1$–$C_6$)alkyl with the proviso that at least one of the ortho or para positions of Ar is substituted;

$R^1$ is hydrogen, halogen, trifluoromethyl, carboxamide, carboxylate, $C_1$–$C_6$ alkyl, $C_3$–$C_7$ cycloalkyl, or ($C_1$–$C_6$ alkyl)-$G^1$—$R^6$ wherein $G^1$ is nitrogen, oxygen or sulfur and $R^6$ is hydrogen, $C_3$–$C_7$ cycloalkyl, or $C_1$–$C_6$ alkyl;

$R^2$ and $R^3$ are taken together, and represent —CH=A—CH=CH—, wherein

A is $CR^8$;

$R^8$ is —($C_1$–$C_6$ alkyl)-$NR^9R^{9'}$; and $R^9$ and $R^{9'}$ independently represent hydrogen or ($C_1$–$C_6$) alkyl;

$R^4$ and $R^5$ are the same or different and represent hydrogen hydroxy, $C_1$–$C_6$ alkoxy($C_1$–$C_6$)alkyl, hydroxy($C_1$–$C_6$) alkyl, $C_3$–$C_7$ cycloalkyl, or $C_1$–$C_6$ alkyl; or phenyl, 2-, 3-, or 4-pyridyl, 2- or 3-thienyl, or 2-, 4-, or 5-pyrimidinyl, each of which is optionally mono- or disubstituted with halogen, hydroxy, $C_1$–$C_6$ alkyl, $C_3$–$C_7$ cycloalkyl, or $C_1$–$C_6$ alkoxy; or $R^4$ and $R^5$ together represent —($C_2$–$C_3$)—$G^3$—($C_1$–$C_3$)— where $G^3$ is methylene, 1,2 phenylene, oxygen, sulfur or $NR^{10}$; and $R^{10}$ is $C_1$–$C_6$ alkyl, $C_3$–$C_7$ cycloalkyl, phenyl, 2-, 3-, or 4-pyridyl, 2- or 3-thienyl, or 2-, 4- or 5-pyrimidyl.

12. A compound according to claim 2, wherein Ar is 2,4,6-trimethylphenyl.

13. A compound according to claim 2, wherein $R^4$ and $R^5$ independently represent hydrogen, $C_1$–$C_6$ alkoxy($C_1$–$C_6$) alkyl, $C_3$–$C_7$ cycloalkyl, or $C_1$–$C_6$ alkyl.

* * * * *